United States Patent [19]

Suzuki et al.

[11] 4,016,100
[45] Apr. 5, 1977

[54] METHOD OF PREPARING A CONTROLLED RELEASE LIQUID PHARMACEUTICAL COMPOSITION

[75] Inventors: Akira Suzuki, Takatsuki; Hiroshi Miura, Neyagawa; Saburo Matsuda, Kyoto; Takashi Ohsawa, Ibaragi, all of Japan

[73] Assignee: Tanabe Seiyaku Co., Ltd., Osaka, Japan

[22] Filed: Jan. 26, 1976

[21] Appl. No.: 652,212

[30] Foreign Application Priority Data

Jan. 27, 1975 Japan .................................. 50-11751

[52] U.S. Cl. .................................. 252/316; 424/19; 424/36; 427/3; 427/398 B
[51] Int. Cl.² ...................... B01J 13/02; A61K 9/52
[58] Field of Search ............... 252/316; 424/19, 36; 427/3, 398 B

[56] References Cited

UNITED STATES PATENTS 3,056,728  10/1962  Ohtaki ........................ 424/36 X
3,780,195  12/1973  Balassa ....................... 252/316 X

OTHER PUBLICATIONS

Chemical Abstracts, vol. 81, 1974, p. 324, 96409m.

*Primary Examiner*—Richard D. Lovering
*Attorney, Agent, or Firm*—Bierman & Bierman

[57] ABSTRACT

A pharmaceutical composition is prepared by the steps of dispersing a phospholipid uniformly in water to give an aqueous phospholipid dispersion, adding a medicament to the aqueous dispersion, freezing the thus-obtained aqueous dispersion, thereby entrapping the medicament in the lipid spherules, and then thawing the frozen dispersion to give an aqueous suspension of the medicament entrapped in the lipid spherules having a diameter of less than 5.0 μ. The pharmaceutical composition prepared above is used as a controlled release pharmaceutical preparation.

11 Claims, 2 Drawing Figures

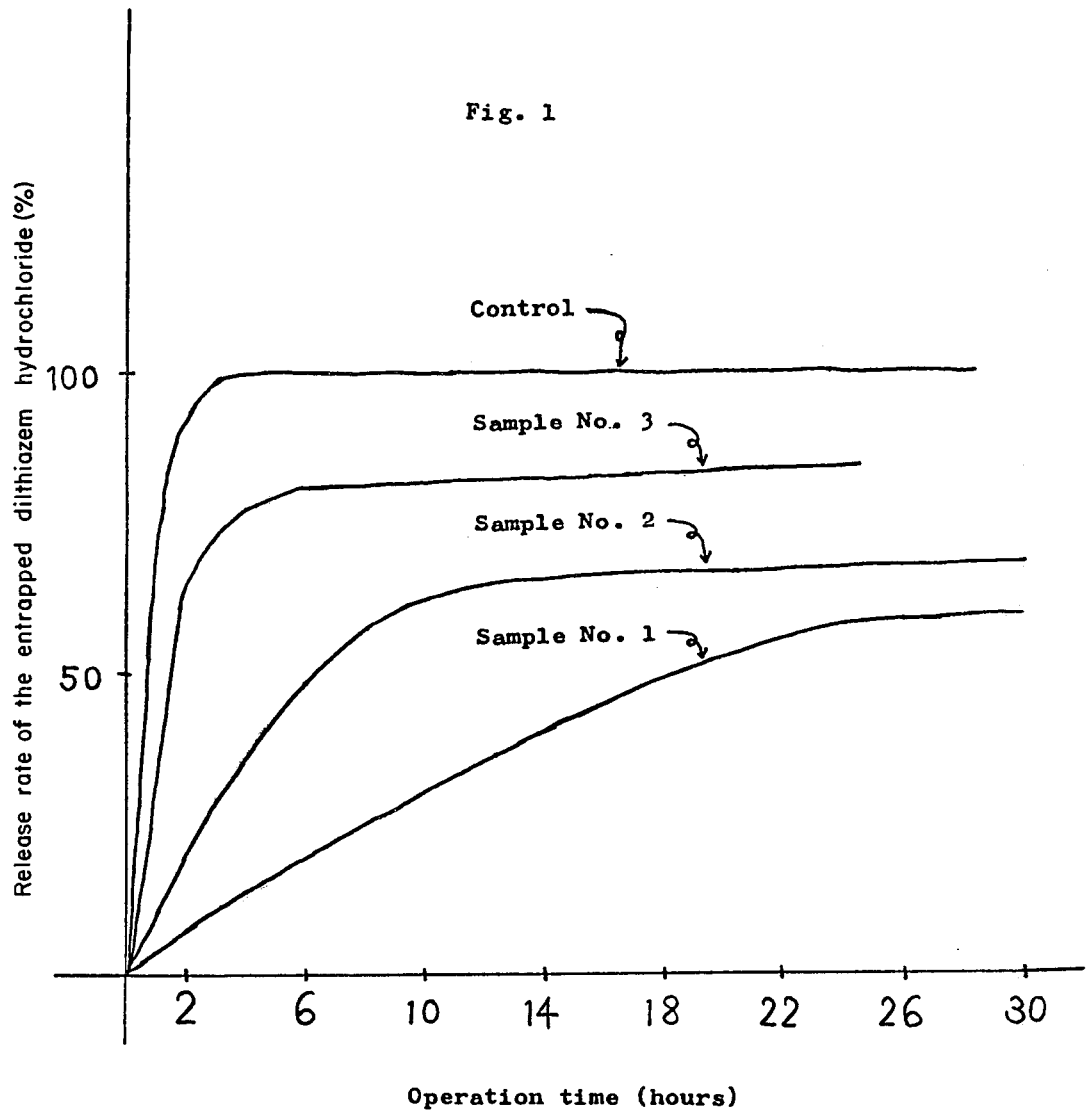

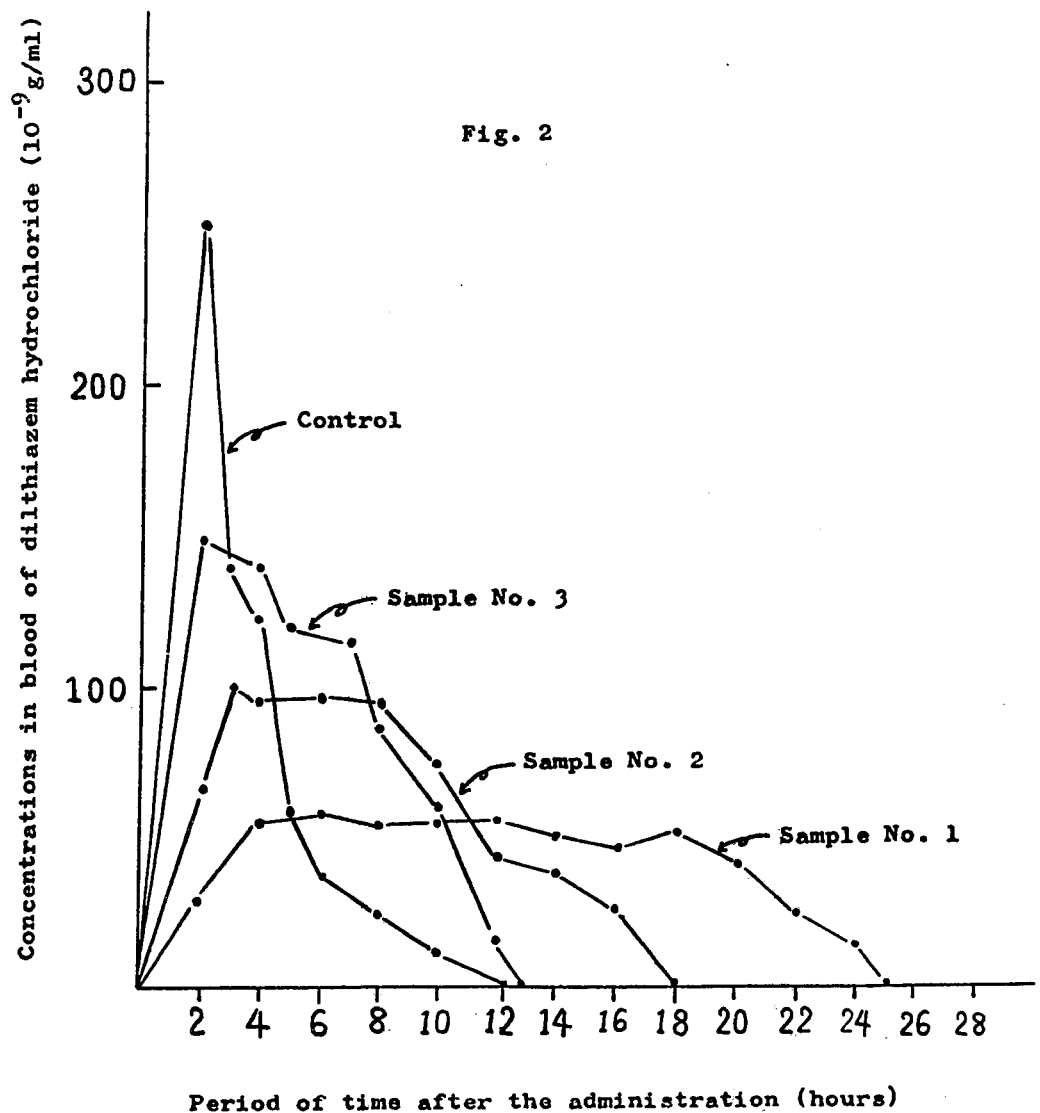

METHOD OF PREPARING A CONTROLLED RELEASE LIQUID PHARMACEUTICAL COMPOSITION

This invention relates to a novel method of preparing a controlled release pharmaceutical composition. More particularly, it relates to a method of preparing an aqueous suspension of a medicament entrapped in spherules of a phospholipid.

Methods of entrapping organic compounds in spherules or particles of a phospholipid have been known. For example, glucose is incorporated into the liposomal structure of a phospholipid by dissolving the phospholipid in chloroform, removing chloroform from the solution under reduced pressure to form a film of the phospholipid on the wall of a container, adding an aqueous glucose solution to the container, and then dispersing the phospholipid into the glucose solution under agitation with a Vortex mixer [Biochim. Biophys. Acta, 150, 655–665 (1968)]. However, this method is disadvantageous in that the chloroform used therein is inevitably entrapped in the lipid spherules and it is almost impossible to remove the chloroform therefrom. This is also disadvantageous in that the aqueous lipid dispersion prepared must be sterilized by heating prior to using it as a pharmaceutical preparation for injection, and the sterilization causes breakdown of the liposomal structure thereof. Further, the size of the lipid spherules of the aqueous lipid dispersion varies over a wide range, from a few millimeters to a several hundred angstroms.

We have now found that a medicament can be entrapped or incorporated into the liposomal structure of a phospholipid by adding the medicament to an aqueous phospholipid dispersion and then freezing the aqueous lipid dispersion. We have also found that the lipid spherules in the aqueous suspension obtained by thawing the above-mentioned frozen lipid dispersion have a substantially uniform diameter of less than 5.0 $\mu$. We have further found that the amount of medicament to be entrapped with the phospholipid and the rate of release of the entrapped medicament from the phospholipid can be controlled by changing the quantitative ratio of the medicament of the phospholipid used.

One object of the present invention is to provide a controlled or sustained release pharmaceutical composition which can release a medicament over a prolonged period of time according to a pre-selected release pattern. Another object of the invention is to provide a method of preparing an aqueous suspension of a medicament entrapped in phospholipid spherules having a substantially uniform diameter of less than 5.0 $\mu$. Another object is to provide a method which makes it possible to entrap a medicament in phospholipid spherules by simple steps without using an organic solvent such as chloroform. A further object of the invention is to provide a method which makes it possible to prepare a liquid pharmaceutical composition under aseptic conditions. Other objects of the present invention will be apparent from the description which follows.

According to the present invention a controlled release pharmaceutical composition can be prepared by dispersing a phospholipid uniformly in water to produce an aqueous phospholipid dispersion, adding a medicament to, or dissolving it in, the aqueous phospholipid dispersion, freezing the thus-obtained medicament dispersion, thereby entrapping the medicament in the lipid spherules, and then thawing the frozen dispersion to give an aqueous suspension of the medicament entrapped in the lipid spherules.

Suitable examples of the phospholipid which are used in the present invention include egg-yolk phospholipids, soybean phospholipids, phosphatidyl choline, phosphatidyl ethanolamine, sphingomyelin, phosphatidyl serine, dipalmitoyl lecithin and mixtures thereof. The preferred amount of the phospholipid which is used in the present invention is 0.001 to 0.2 g, especially 0.005 to 0.08 g, per ml of water.

The aqueous phospholipid dispersion can be readily prepared. For example, the phospholipid is added to water and the mixture is treated with a homongenizer to disperse the phospholipid uniformly in water.

The aqueous phospholipid dispersion may also be prepared by adding the phospholipid to water, stirring the mixture with a homomixer to disperse the phospholipid roughly in water, and then treating the mixture with a homogenizer. Conventional homogenizers can be employed in the present invention; for example, devices in which dispersion is effected by forcing the mixture to be dispersed through a small orifice under high pressure. Suitable examples of such devices are disclosed in "EMULSIONS: THEORY and PRACTICE" pages 227–230(1957) (published by Reinhold Publishing Corp., New York, U.S.A.) hereby incorporated by reference. In order to produce lipid spherules or particles having a diameter of less than 5.0 $\mu$, it is preferred to carry out the above-mentioned step of the invention under a pressure of more than 200 kg/cm$^2$, especially 350 to 550 kg/cm$^2$.

Alternatively, the aqueous phospholipid dispersion of the invention may be prepared by adding the phospholipid to water, and then treating the mixture with a conventional ultrasonic emulsator such as any one of those disclosed in "EMULSIONS: THEORY and PRACTICE" pages 234–238 (1957) (published by Reinfold Publishing Corp., New York, U.S.A.) hereby incorporated by reference. The suitable size of lipid spherules or particles in the aqueous phospholipid dispersion is less than 5.0 $\mu$ in diameter. Further, the aqueous phospholipid dispersion obtained above may be, if necessary, filtered through a membrane filter having a pore size of 0.1 to 5.0 $\mu$, preferably 0.22 to 0.8 $\mu$.

A medicament is then added to or dissolved in the aqueous phospholipid dispersion obtained above. This step can be conducted in any conventional matter; for example, either by adding the medicament directly to the aqueous phospholipid dispersion under stirring, or by adding the medicament to water and then mixing the solution with the aqueous phospholipid dispersion.

Any pharmaceutically active organic compound may be used as the medicament of the present invention. Further, a water-soluble medicament (a water-soluble pharmaceutically active organic compound) is especially suitable for the present invention. Thus, for example, the medicament may be symphathomimetic agent such as amphetamine sulfate, epinephrine hydrochloride or ephedrine hydrochloride; antispasmodics such as hyosthiamine, atropine, scopolamine hydrobromide, timepidium bromide [Chemical name: di-(2-thienyl)-(N-methyl-5-methoxy-3-piperidyliden)-methane methyl-bromide]; bronchodilators such as tretoquinol hydrochloride [Chemical name: 1-1-(3,4,5-trimethoxybenzyl)-6,7-dihydroxy-1,2,3,4-tetrahydroisoquinoline hydrochloride] or isoproterenol hydrochloride; vasodilators such as dilthiazem hydrochloride [Chemical name: α-3-acetoxy-cis-2,3-dihydro-5[2-(dimethyl-aminoethyl]-2-(p-methoxyphenyl)-1,5-benzodiazepin-4(5H)-one hydrochloride] or dipyridamole; hemostatics such as carbazo-chrome sodium sulfate [Chemical name: sodium 1-methyl-5-semi-carbazono-6-oxo-2,3,5,6-tetrahydroindol-3-sulfonate]; vitamins such as bisbutylthiamine [Chemical name: N,N'-{dithiobis [2-(2-butyroylethyl)-1-methylvinylene]}bis{ N-[(4-amino-2-methyl-5-pyrimidinyl)methyl]}formamide]: hormones such as insulin; and antibiotics such as amino benzylpenicillin, α-phenoxypropylpenicillin or α-carboxybenzylpenicillin. The amount of the medicament which is added to the aqueous phospholipid dispersion is not critical and may vary over a wide range depending on the medicament used, its manner of administration, and other factors. Generally, however, it is preferred to use 0.01 to 1.0 g, especially 0.04 to 0.3 g, per g of the phospholipid.

The thus-obtained aqueous dispersion containing the phospholipid and the medicament is then frozen, whereby the medicament is entrapped or encapsulated in the lipid spherules of the phospholipid. This freezing step is preferably carried out at a temperature below $-5°$ C (i.e., $-5°$ to $-40°$ C), especially $-10°$ to $-30'$ C. The amount of the medicament to be entrapped or encapsulated in the phospholipid spherules can be easily controlled by changing the quantitative ratio of the phospholipid to the medicament. The amount of said medicament to be entrapped can be increased by increasing the quantitative ratio of the phospholipid to the medicament, and vice versa.

The aqueous suspension of the present invention (i.e., the aqueous suspension of the medicament entrapped in the phospholipid spherules) can be obtained by thawing or liquifying the frozen phospholipid dispersion obtained in the above-mentioned step. Said thawing or liquification is carried out by allowing the frozen phospholipid dispersion to stand at a temperature of 5° to 40° C, especially about 15° to 25° C. The aqueous suspension thus obtained comprises finely divided spherules of the phospholipid, the medicament entrapped in the lipid spherules thereof, and water. The lipid spherules in said aqueous suspension have a substantially uniform diameter of less than 5.0 $\mu$, preferably 0.1 to 2.0 $\mu$.

If required, the medicament containing phospholipid may be further separated from the aqueous suspension of the present invention. The separation of the entrapped medicament from the aqueous suspension is carried out in a conventional manner such as by centrifugation thereof.

As is illustratively shown in the following experiments, the larger the amount of the entrapped medicament, the slower the rate of release of the medicament. Moreover, the rate of release of the medicament from the aqueous suspension of the present invention (i.e., the aqueous suspension of the medicament entrapped in the lipid spherules) can be easily controlled by changing the amount of the medicament added to the aqueous phospholipid disperson (i.e., the dispersion which is obtained by dispersing the phospholipid in water). Further, when the aqueous suspension of the present invention is administered to gastrointestinal tracts, muscles, blood vessels or other tissues, the medicament is released therefrom into said tissues constantly for period as short as 30 minutes, or as long as 40 hours or longer according to a preselected release pattern. In view of the foregoing, the aqueous suspension of the present invention can be used per se as a controlled or sustained release liquid pharmaceutical composition which is suitable for injection or oral administration.

If desired, other pharmaceutical preparations; e.g., suppositories, may be prepared by separating the trapped medicament from the aqueous suspension of the invention and then admixing it with suitable excipients such as diluents, binders or extenders. In all events, since the phospholipid used in encapsulation of the medicament retards the release rate of the medicament, the pharmaceutical compositions prepared as above may preferably be used as sustained release pharmaceutal preparations.

FIG. 1 is a graph showing the release rate of entrapped dilthiazem hydrochloride in per cent vs. operation time in hours.

FIG. 2 is a graph showing concentrations in blood of dilthiazem hydrochloride ($10^{-9}$ g/ml) vs. period of time after the administration (hours).

Practical and presently-preferred embodiments of the present invention are illustratively shown in the following Examples. The terminology "water" employed in the following Experiments and Examples is "distilled water for injection" which meets with the standard of U.S. Pharmacopoeia, Eighteenth Edition.

EXPERIMENTS

1. Sufficient water is added to 100, 60 or 20 g of egg-yolk phospholipids ( a mixture of 63 w/w % of phosphatidyl choline, 23 w/w % of phosphatidyl ethanolamine and 8 w/w % of sphyngomyelin) to bring the total volume to 1 liter. The mixture is stirred with a homomixer (Tokusyu Kika Kogyo Co., Ltd., Model 4C). Then, the mixture is homogenized with an emulsifier (Manton-Gaulin Manufacturing Co., Inc., Model 15M) under a pressure of 400 kg/cm² for 30 minutes, whereby the egg-yolk phospholipids are dispersed uniformly in the water. The aqueous phospholipid dispersion thus obtained is filtered through a membrane filter (pore size: 0.45 $\mu$ in diameter). 20 g of dilthiazem hydrochloride and 18 g of sodium chloride are dissolved in sufficient water to bring the total volume to 1 liter, and the dilthiazem solution is filtered through a membrane filter (pore size: 0.45 $\mu$ in diameter). 850 ml of the aqueous phospholipid dispersion is mixed with 805 ml of the dilthiazem solution and sterilized at 115° C for 30 minutes (The aqueous dispersion thus obtained is hereinafter referred to as Sample No. 1', 2' or 3'). Then, the aqueous dispersion (i.e., Sample No. 1', 2' or 3') is allowed to stand at $-20°$ C in a freezer overnight. The frozen dispersion is thawed by allowing it to stand at room temperature. An aqueous suspension of dilthiazem hydrochloride entrapped in the phospholipid spherules is thereby obtained. The suspension thus obtained is hereinafter referred to as Sample No. 1, 2 or 3.

For comparison, a suspension of dilthiazem hydrochloride entrapped in lipid spherules is prepared in accordance with the method disclosed in Biochemistry, 8, 4149–4158 (1969). That is, 20 g of egg-yolk phospholipids are dissolved in 10 ml of chloroform. The solution is placed in a round-bottomed flask and evaporated under reduced pressure, whereby a film of egg-yolk phospholipids is formed on the wall of the flask. The flask is placed in a desiccator to remove the chloroform. 4 g of dilthiazem hydrochloride are dissolved in 40 ml of water, and the solution is poured into the flask. The flask is shaken rotatively until the film of egg-yolk phospholipids is no longer detectable on the wall of the flask. An aqueous suspension of dilthiazem hydrochloride entrapped in phospholipids is no longer detectable on the wall of the flask. An aqueous suspension of dilthiazem hydrochloride trapped in phospholipid spherules is obtained. This suspension is hereinafter referred to as Sample No. 4.

The size of the spherules of particles of egg-yolk phospholipids in each one of the suspensions obtained above is observed microscopically. The results are shown in Table 1.

TABLE 1

| Sample Nos. | Amount of egg-yolk phospholipids contained in the sample (w/v %) | Size of lipid spherules ($\mu$in diameter) |
| --- | --- | --- |
| 1 | 5 | 0.1 – 2.0 |
| 2 | 3 | 0.1 – 0.8 |
| 3 | 1 | 0.1 – 1.5 |
| 4 | 5 | 0.5 – 50 |

2. The aqueous dispersion (i.e., Sample No. 1', 2' or 3') or the aqueous suspension (i.e., Sample No. 1, 2 or 3) obtained in paragraph (1) is centrifuged to remove the phospholipid spherules. The amount of dilthiazem hydrochloride in the supernatant solution is estimated by ultraviolet absorption assay, and the amount of dilthiazem hydrochloride entrapped in the spherules of egg-yolk phospholipids is calculated therefrom. The results are shown in Table 2.

TABLE 2

| Sample Nos. | Amount of egg-yolk phospholipids contained in the samples (w/v %) | Amount of dilthiazem entrapped in lipid spherules/Amount of dilthiazem contained in the sample (w/w %) |
| --- | --- | --- |
| 1' | 5 | 5 |
| 2' | 3 | 2 |
| 3' | 1 | 1 |
| 1 | 5 | 76 |
| 2 | 3 | 41 |
| 3 | 1 | 20 |

3. 2 ml of the aqueous suspension (Sample No. 1, 2 or 3) obtained in paragraph (1) are dialyzed at 30° C through a cellophane membrane against 28 ml of a physiological saline solution. The amount of dilthiazem hydrochloride in the dialysate is estimated at intervals by ultraviolet absorption assay, and the rate of release of the entrapped dilthiazem hydrochloride from egg-yolk phospholipids is calculated by the following formula:

$$100 \times \left[ \frac{\text{Amount of dilthiazem hydrochloride released into the dialysate}}{\text{Amount of dilthiazem hydrochloride contained in the sample (e.g., Sample No. 1, 2 or 3)}} \right]$$

A physiological saline solution containing 10 mg/ml of dilthiazem hydrochloride is employed as a control. The results are shown in Table 3 and FIG. 1.

TABLE 3

| Operation time (hours) | Release rate of the entrapped dilthiazem hydrochloride (%) | | | |
| --- | --- | --- | --- | --- |
| | Samples | | | |
| | No. 1 | No. 2 | No. 3 | Control |
| 1 | 4 | 11 | 34 | 70 |
| 2 | 7 | 20 | 66 | 95 |
| 3 | 10 | 28 | 75 | 99 |
| 4 | 13 | 35 | 79 | 100 |
| 6 | 20 | 50 | 83 | 100 |
| 10 | 31 | 64 | 84 | 100 |
| 14 | 42 | 68 | 85 | 100 |
| 18 | 51 | 69 | 86 | 100 |
| 22 | 58 | 70 | 87 | 100 |
| 26 | 61 | 71 | — | 100 |

4. One ml of the aqueous suspension (Sample No. 1, 2 or 3) obtained in paragraph (1) is administered to dogs (i.e., beagles) intramuscularly, and the concentrations in blood of dilthiazem hydrochloride is estimated with the passage of time. In the control group, one ml of an aqueous isotonic solution containing 10 mg/ml of dilthiazem hydrochloride is administered to dogs (i.e., beagles) in the same manner as described above. The results are shown in Table 4 and FIG. 2.

TABLE 4

| Period of time after the administration (hours) | concentrations in blood of dilthiazem hydrochloride ($10^{-9}$ g/ml) | | | |
| --- | --- | --- | --- | --- |
| | Samples | | | |
| | No. 1 | No. 2 | No. 3 | Control |
| 2 | 28 | 67 | 152 | 254 |
| 4 | 56 | 98 | 142 | 125 |
| 6 | 60 | 99 | 120 | 36 |
| 8 | 55 | 97 | 89 | 24 |
| 10 | 56 | 76 | 62 | 10 |
| 12 | 57 | 44 | 16 | 0 |
| 14 | 52 | 39 | 0 | — |
| 16 | 48 | 26 | — | — |
| 18 | 53 | 0 | — | — |
| 20 | 42 | — | — | — |
| 24 | 12 | — | — | — |

As seen in the Table, the medicament-containing phospholipids of the present invention provide a sustained release of the medicament over a period of up to about 12 to about 24 hours.

EXAMPLE 1

Sufficient water is added to 60 g of egg-yolk phospholipids to bring the total volume to 1.5 liters. The mixture is stirred with a homomixer (Tokusyu Kika Kogyo Co., Ltd., Model 4C). Then, the mixture is homogenized with an emulsifier (Manton-Gaulin Manufacturing Co., Inc., Model 15M) under a pressure of 400 kg/cm² for 30 minutes, whereby an aqueous phospholipid dispersion is obtained. 10 g of tretoquinol hydrochloride are dissolved in enough water to bring the total volume to 1 liter. 950 ml of the aqueous phospholipid dispersion is mixed with 950 ml of the tretoquinol solution. The aqueous dispersion thus obtained is allowed to stand at −20° C for 20 hours in a freezer. Then, the frozen dispersion is thawed by allowing it to stand at room temperature. An aqueous suspension of tretoquinol hydrochloride entrapped in phospholipid spherules is thereby obtained. The size of the spherules of egg-yolk phospholipids in the suspension is within the range of 0.1–2.0 $\mu$ in diameter.

EXAMPLE 2

Sufficient water is added to 100 g of egg-yolk phospholipids to bring the total volume to 1 liter. The mixture is stirred with a homomixer (Tokusyu Kika Kogyo Co., Ltd., Model 4C). Then, the mixture is homogenized with an emulsifier (Manton-Gaulin Manufacturing Co., Inc., Model 15M) under a pressure of 300 kg/cm$^2$ for 30 minutes, whereby an aqueous phospholipid dispersion is obtained. 20 g. of diphenhydramine hydrochloride and 18 g of sodium chloride are dissolved in enough water to bring the total volume to 1 liter. 850 ml of the aqueous phospholipid dispersion is mixed with 850 ml of the diphenhydramine solution. The aqueous dispersion thus obtained is filtered through a membrane filter (pore size: 0.45 μ in diameter). The filtrate is sterilized at 120° C for 20 minutes, and then allowed to stand at −20° C for 20 hours in a freezer. The frozen dispersion thus obtained is thawed by allowing it to stand at room temperature. An aqueous suspension of diphenhydramine hydrochloride entrapped in phospholipid spherules is thereby obtained. The size of the spherules of the egg-yolk phospholipids in the suspension is within the range of 0.1–2.0 μ in diameter.

EXAMPLE 3

Sufficient water is added to 10 g of soybean phospholipids to bring the total volume to 1 liter. The mixture is stirred with a homomixer (Tokusyu Kika Kigyo Co., Ltd., Model 4C). Then, the mixture is homogenized with an emulsifier (Manton-Gaulin Manufacturing Co., Inc., Model 15M) under a pressure of 400 kg/cm$^2$ for 30 minutes, and filtered by a membrane filter (pore size: 0.45 μ in diameter). An aqueus phospholipid dispersion is thereby obtained. Crystalline insulin (4000 units) is dissolved in a phosphate buffer solution (pH 7.2) to bring the total volume to one liter, and the solution is filtered through a membrane filter (pore size: 0.45 μ in diameter). 850 ml of the aqueous phospholipid dispersion is mixed with 850 ml of the insulin solution. The aqueous dispersion thus obtained is allowed to stand at −20° C for 20 hours in a freezer. The frozen dispersion thus obtained is thawed by allowing to stand at room temperature. An aqueous suspension of insulin entrapped in phospholipid spherules is thereby obtained. The size of the spherules of the soybean phospholipids in suspension is within the range of 0.1–1.8 μ in diameter.

EXAMPLE 4

Sufficient water is added to 100 g of phosphatidyl choline to bring the total volume to 1 liter. The mixture is stirrred with a homomixer (Tokusyu Kika Kogyo Co., Ltd., Model 4C). Then, the mixture is homogenized with an emulsifier (Manton-Gaulin Manufacturing Co., Inc., Model 15M) under a pressure of 400 kg/cm$^2$ for 30 minutes, whereby an aqueous phospholipid dispersion is obtained. 10 g of timepidium bromide and 18 g of sodium chloride are dissolved in enough water to bring the total volume to 1 liter. 850 ml of the aqueous phospholipid dispersion is mixed with 850 ml of the timepidium bromide solution. The aqueous dispersion thus obtained is filtered through a membrane filter (pore size: 0.45 μ in diameter). The filtrate is sterilized at 115° C for 30 minutes, and then allowed to stand at −20° C for 20 hours in a freezer. The frozen dispersion thus obtained is thawed by allowing it to stand at room temperature. An aqueous suspension of timepidium bromide entrapped in phospholipid spherules is thereby obtained. The size of the spherules of phosphatidyl choline in the suspension is within the range of 0.2–2.0 μ in diameter.

EXAMPLE 5

Sufficient water is added to 80 g of egg-yolk phospholipids to bring the total volume to 1 liter. The mixture is stirred with a homomixer (Tokusyu Kika Kogyo Co., Ltd., Model 4C). Then, the mixture is homogenized with an emulsifier (Manton-Gaulin Manufacturing Co., Inc., Model 15M) under a pressure of 500 kg/cm$^2$ for 30 minutes, whereby an aqueous phospholipid dispersion is obtained. 20 g of bisbutylthiamine and 18 g of sodium chloride are dissolved in 0.01 N-hydrochloric acid to bring the total volume to 1 liter. 850 ml of the aqueous phospholipid dispersion is mixed with 850 ml of the bisbutylthiamine solution. The aqueous dispersion thus obtained is filtered through a membrane filter (pore size: 0.45 μ in diameter). The filtrate is sterilized at 115° C for 30 minutes, and then allowed to stand at −20° C for 20 hours in a freezer. The frozen dispersion thus obtained is thawed by allowing it to stand at room temperature. An aqueous suspension of bisbutylthiamine entrapped in phospholipid spherules is thereby obtained. The size of the spherules of the egg-yolk phospholipids in the suspension is within the range of 0.2–2.0 μ in diameter.

What is claimed is:

1. A method of preparing a controlled release pharmaceutical composition, which comprises the steps of dispersing a phospholipid uniformly in water to give an aqueous phospholipid dispersion having lipid spherules, adding a medicament to the aqueous phospholipid dispersion to form a medicament dispersion, freezing said medicament dispersion thereby entrapping the medicament in the lipid spherules, and then thawing the frozen dispersion to give an aqueous suspension of the medicament entrapped in said lipid spherules, said spherules having a diameter of less than 5.0 μ.

2. The method according to claim 1, wherein the phospholipid is selected from the group consisting of egg-yolk phospholipids, soybean phospholipids, phosphatidyl choline, phosphatidyl ethanolamine, sphingomyelin, phosphatidyl serine and dipalmitoyl lecithin.

3. The method according to claim 1, wherein the phospholipid is egg-yolk phospholipids.

4. The method according to claim 1, wherein the phospholipid is soybean phospholipids.

5. The method according to claim 1, wherein the phospholipid is employed in an amount of 0.001 to 0.2 g per ml of said water, and the medicament is employed in an amount of 0.01 to 1.0 g per g of the phospholipid.

6. The method according to claim 1, wherein said freezing is carried out at a temperature below −5° C and said thawing is carried out by allowing it to stand at a temperature of 5° to 40° C.

7. The method according to claim 1, further including the step of centrifuging the aqueous suspension to separate the entrapped medicament therefrom.

8. A method of preparing a controlled release pharmaceutical composition which comprises dispersing 0.001 to 0.2 g of a phospholipid per ml of water to give an aqueous phospholipid dispersion having lipid spherules, addng 0.01 to 1.0 g of a medicament per g of said phospholipid to the aqueous dispersion to form a medicament dispersion, freezing said medicament dispersion at a temperature below −5° C, thereby entrapping the medicament in the lipid spherules, and then allowing the frozen dispersion to stand at a temperature of 5° to 40° C to give an aqueous suspension of the medicament entrapped in the lipid spherules, said spherules having a diameter of less than 5.0 μ.

9. The method according to claim 8, wherein the phospholipid is egg-yolk phospholipids.

10. The method according to claim 8, wherein the phospholipid is soybean phospholipids.

11. The method according to claim 8, further including the step of centrifuging the aqueous suspension to separate the trapped medicament therefrom.

* * * * *